(12) United States Patent
Nierich

(10) Patent No.: US 10,792,186 B2
(45) Date of Patent: Oct. 6, 2020

(54) ASSEMBLY, ESOPHAGUS CATHETER AND METHOD FOR CONTROLLING A TEMPERATURE OF AT LEAST A PART OF A PERSON, IN PARTICULAR THE BRAIN OF THE PERSON

(71) Applicant: Gelanus B.V., Hattem (NL)

(72) Inventor: Arno Pieter Nierich, Hattem (NL)

(73) Assignee: GELANUS B.V., Hattem (NL)

( * ) Notice: Subject to any disclaimer, the term of this patent is extended or adjusted under 35 U.S.C. 154(b) by 391 days.

(21) Appl. No.: 15/316,084

(22) PCT Filed: Jun. 2, 2015

(86) PCT No.: PCT/EP2015/062302
§ 371 (c)(1),
(2) Date: Dec. 2, 2016

(87) PCT Pub. No.: WO2015/185577
PCT Pub. Date: Dec. 10, 2015

(65) Prior Publication Data
US 2017/0105871 A1    Apr. 20, 2017

(30) Foreign Application Priority Data
Jun. 2, 2014  (EP) .................................. 14170783

(51) Int. Cl.
*A61F 7/12*         (2006.01)
*A61M 16/04*    (2006.01)
(Continued)

(52) U.S. Cl.
CPC ................ *A61F 7/123* (2013.01); *A61B 8/12* (2013.01); *A61B 8/488* (2013.01); *A61F 7/12* (2013.01);
(Continued)

(58) Field of Classification Search
CPC ...... A61F 7/12; A61F 7/123; A61F 2007/126; A61F 2007/0002; A61F 2007/0056;
(Continued)

(56) References Cited

U.S. PATENT DOCUMENTS 6,264,679 B1   7/2001   Keller
2001/0044644 A1*  11/2001   Keller ....................... A61F 7/12
                                                                                607/105
(Continued)

FOREIGN PATENT DOCUMENTS

| WO | 0113809 A1 | 3/2001 |
| WO | 0130413 A2 | 5/2001 |
| WO | 2006124702 A2 | 11/2006 |

OTHER PUBLICATIONS

International Search Report and Written Opinion for International application No. PCT/EP2015/062302, dated Nov. 27, 2015.

*Primary Examiner* — Eun Hwa Kim
*Assistant Examiner* — Adam Z Minchella
(74) *Attorney, Agent, or Firm* — Steven M. Koehler; Westman, Champlin & Koehler, P.A.

(57) ABSTRACT

The present invention relates to an assembly for controlling a temperature of at least a part of a person, comprising an esophagus catheter to be inserted into the esophagus of the person for controlling the temperature. The esophagus catheter extends along a longitudinal axis and comprises a proximal heat exchanger defining a first flow direction having a first axial component relative to the longitudinal axis, and a distal heat exchanger defining a second flow direction having a second axial component relative to the longitudinal axis. The esophagus catheter further comprises a plurality of coolant channels each in fluid communication with at least one of the proximal heat exchanger and the distal heat exchanger, and a coolant pump connected or connectable to at least one of the plurality of coolant channels. The assembly is configured to cause simultaneously a coolant flow through the proximal heat exchanger and the distal heat exchanger.

20 Claims, 6 Drawing Sheets

(51) Int. Cl.
*A61M 19/00* (2006.01)
*A61B 8/12* (2006.01)
*A61B 8/08* (2006.01)
*A61F 7/00* (2006.01)

(52) U.S. Cl.
CPC ........ *A61M 16/04* (2013.01); *A61M 16/0409* (2014.02); *A61M 16/0438* (2014.02); *A61M 16/0459* (2014.02); *A61M 16/0463* (2013.01); *A61M 16/0486* (2014.02); *A61M 19/00* (2013.01); *A61F 2007/0002* (2013.01); *A61F 2007/0056* (2013.01); *A61F 2007/0092* (2013.01); *A61M 2205/3375* (2013.01); *A61M 2205/366* (2013.01)

(58) Field of Classification Search
CPC ... A61F 2007/0092; A61B 8/12; A61B 8/488; A61M 16/0409; A61M 16/0438; A61M 16/0459; A61M 16/0486; A61M 16/04; A61M 16/0463; A61M 19/00; A61M 2205/3375; A61M 2205/366
See application file for complete search history.

(56) References Cited

U.S. PATENT DOCUMENTS

| | | | |
|---|---|---|---|
| 2002/0029016 A1 | 3/2002 | Pham | |
| 2002/0151945 A1* | 10/2002 | Gobin | A61F 7/12 607/105 |
| 2003/0195466 A1 | 10/2003 | Pham | |
| 2003/0208156 A1* | 11/2003 | Pham | A61F 7/123 604/113 |
| 2004/0199114 A1* | 10/2004 | Noda | A61F 7/12 604/113 |
| 2006/0276552 A1* | 12/2006 | Barbut | A61F 7/12 514/743 |
| 2007/0123813 A1 | 5/2007 | Barbut | |
| 2008/0004613 A1 | 1/2008 | Barbut | |
| 2008/0086186 A1* | 4/2008 | Takeda | A61F 7/12 607/105 |
| 2008/0249188 A1 | 10/2008 | Barbut | |
| 2009/0177258 A1* | 7/2009 | Takeda | A61M 16/0486 607/105 |
| 2010/0324635 A1* | 12/2010 | Kreck | A61F 7/12 607/105 |
| 2011/0023885 A1* | 2/2011 | Vazales | A61B 1/07 128/207.14 |
| 2011/0028938 A1 | 2/2011 | Barbut | |
| 2012/0083764 A1 | 4/2012 | Barbut | |
| 2014/0076309 A1* | 3/2014 | Takeda | A61F 7/123 128/200.26 |

* cited by examiner

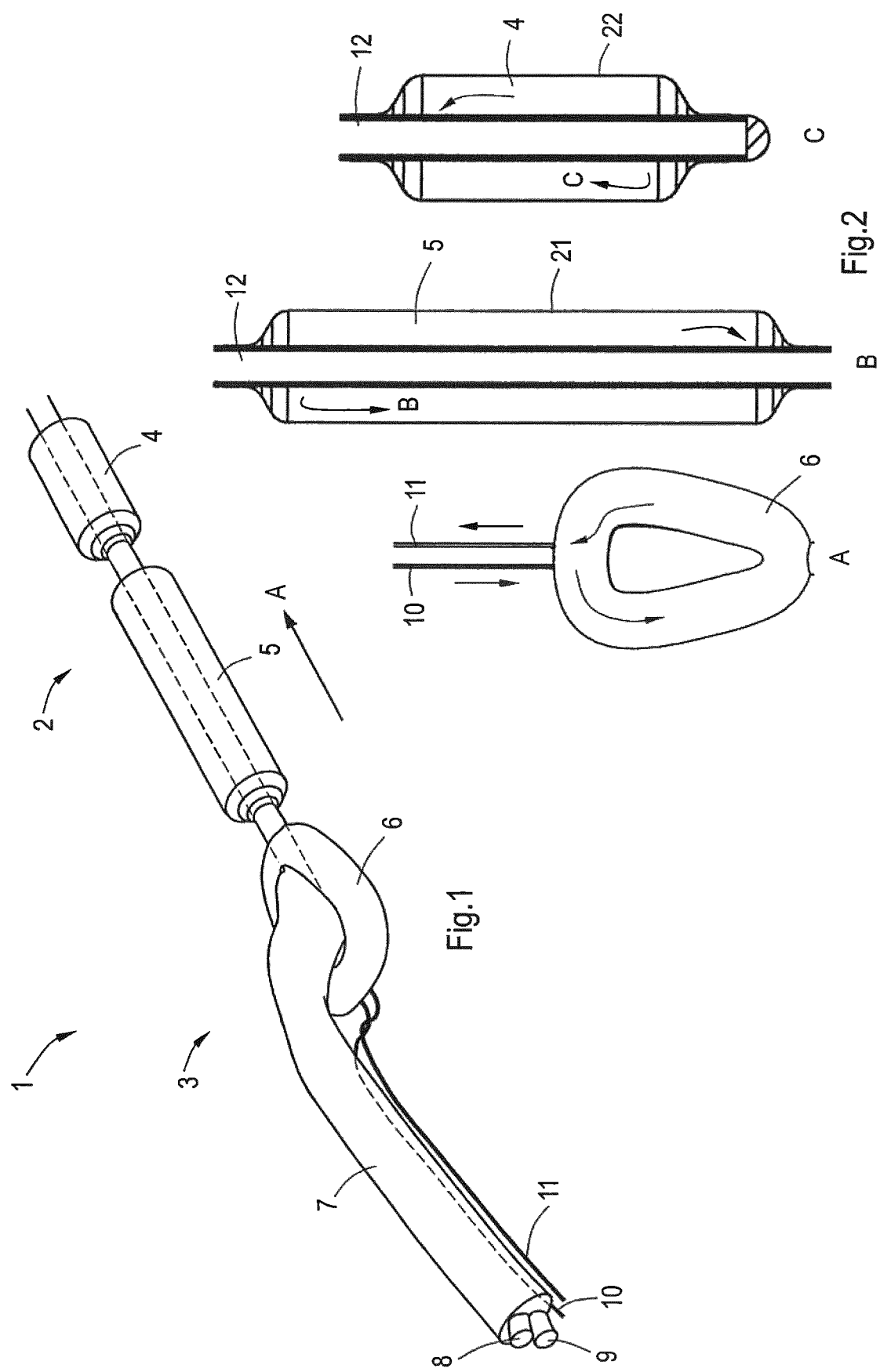

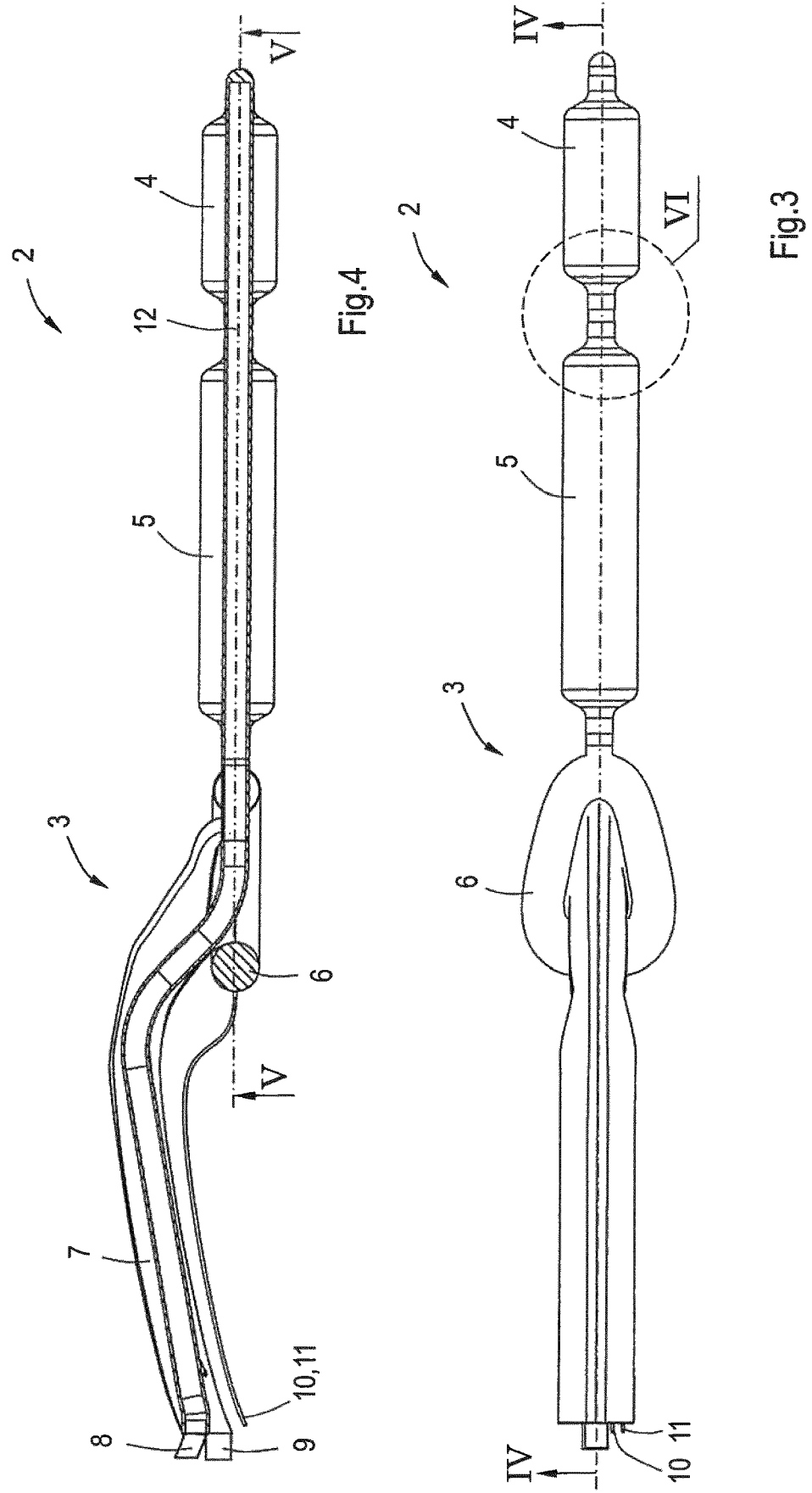

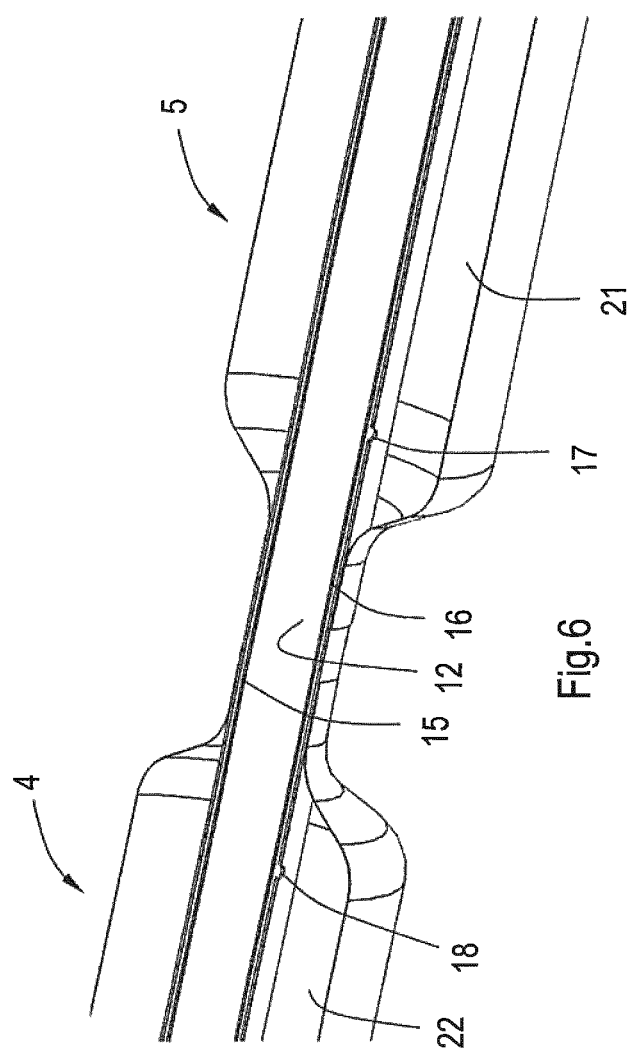
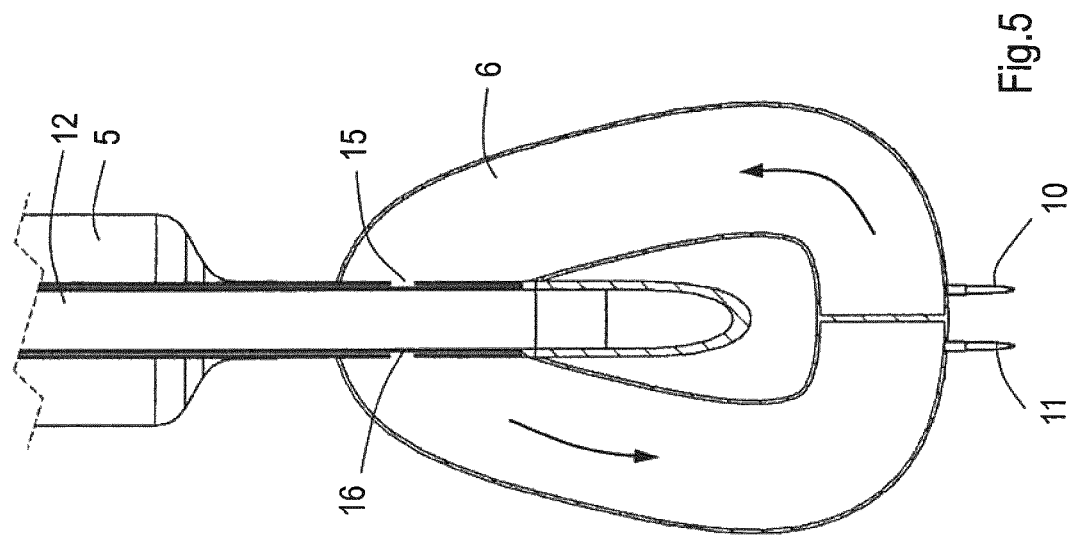

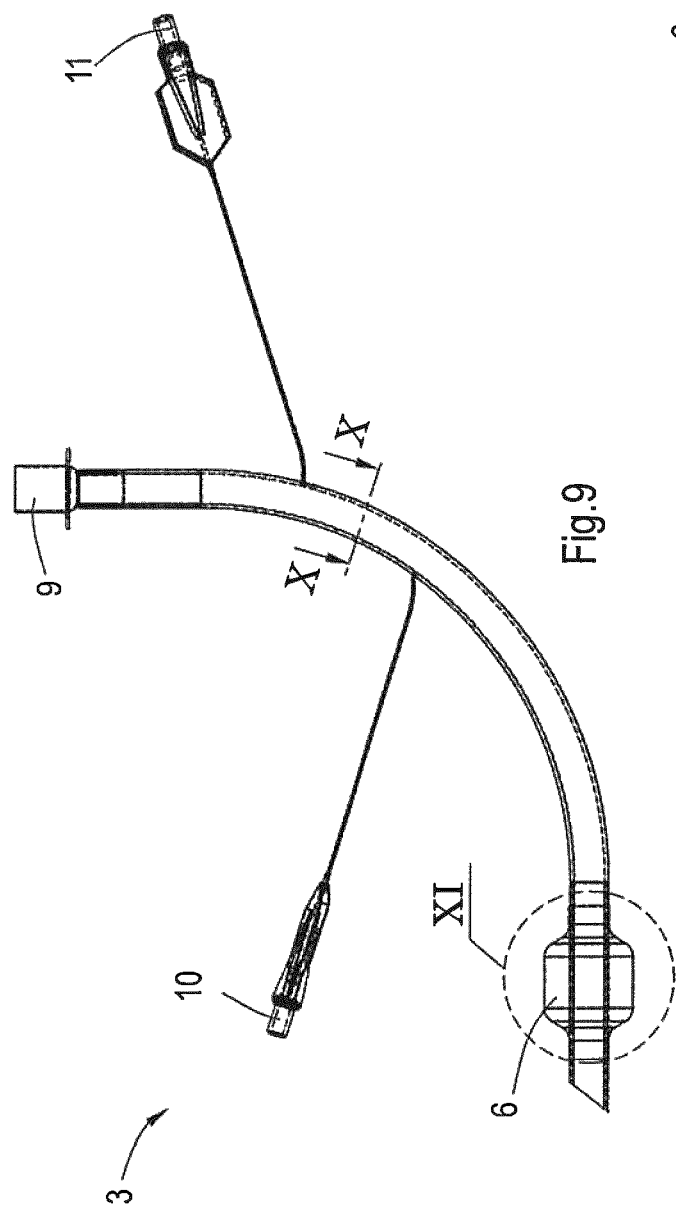
Fig.9
Fig.10
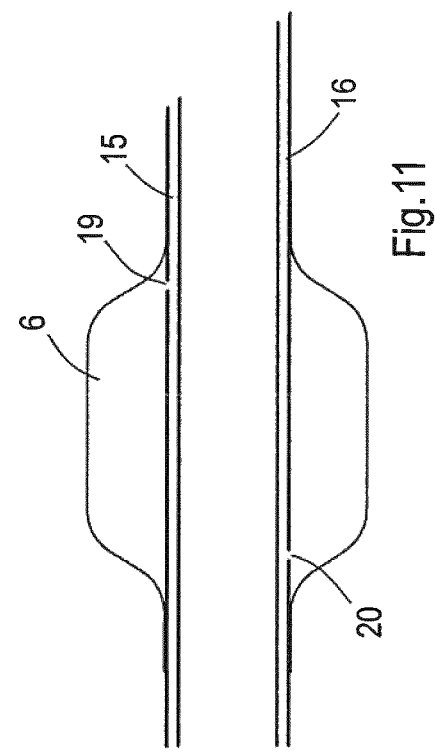
Fig.11

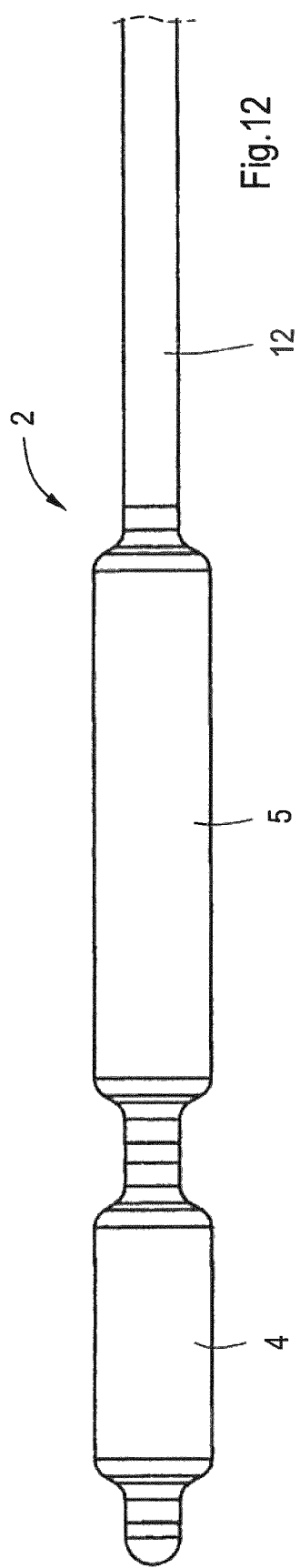

ASSEMBLY, ESOPHAGUS CATHETER AND METHOD FOR CONTROLLING A TEMPERATURE OF AT LEAST A PART OF A PERSON, IN PARTICULAR THE BRAIN OF THE PERSON

The present invention relates to an assembly for controlling a temperature, e.g. cooling, of a part of a person, in particular the brain of the person, for example during or after a cardiac arrest. The present invention further relates to an esophagus catheter and method for controlling a temperature, e.g. cooling, of a part of a person, in particular the brain of the person.

Cardiac arrest is the cessation of circulation of the blood due to a failure of the heart to contract effectively. The failure of the heart to contract effectively reduces the delivery of oxygen and glucose throughout the human body. A lack of oxygen and glucose to the brain of a person may cause loss of consciousness, eventually resulting in abnormal or absent breathing and/or swelling of the brain.

In order to provide a chance of survival and of neurological recovery after cardiac arrest, immediate and decisive treatment is imperative. One kind of treatment that may be applied is therapeutic hypothermia, also called protective hypothermia. In case of a cardiac arrest, a poor blood flow may occur. As a result of the poor blood flow, tissue of for example the brain may get damaged. In order to reduce the risk of tissue getting damaged, therapeutic hypothermia can be applied to the person. Therapeutic hypothermia relates to a medical treatment for lowering a patient's body temperature. Therapeutic hypothermia may be induced by invasive means or by non-invasive means, such as a chilled water blanket or a torso vest and leg wraps in direct contact with the patient's skin.

US 2009/0177258 relates to a brain cooling device and describes that a brain cooling device is provided to cool the brain sufficiently to cool the subcortical tissue in a short time. The device includes a cuff capable of storing therein a cooled fluid and placeable in the esophagus of the patient when inserted orally or transnasally. A tube extends from the cuff for infusing the fluid into the cuff placed in the esophagus from outside the body of the patient and discharging the fluid from the cuff. The cuff has flexibility so as to inflate or deflate in response to infusion or discharge of the fluid and is configured in such a manner that when the fluid is infused therein while placed in the esophagus, the cuff that has been inflated comes into close contact with the inner wall of the esophagus.

It is an object of the invention to provide for an improved assembly for controlling a temperature, e.g. cooling, of at least a part of a person, in particular the brain of the person.

To this end, the assembly according to the invention comprises an esophagus catheter to be inserted into the esophagus of the person for controlling the temperature, for instance cooling, the esophagus catheter extending along a longitudinal axis. The esophagus catheter comprises a proximal heat exchanger defining a first flow direction having a first axial component relative to the longitudinal axis, e.g. a proximal balloon, and a distal heat exchanger defining a second flow direction having a second axial component relative to the longitudinal axis, e.g. a distal balloon. The esophagus catheter further comprises a plurality of coolant channels each in fluid communication with at least one of the proximal heat exchanger and the distal heat exchanger, and a coolant pump, such as a fluid pump or a syringe, which is connected or connectable to at least one of the plurality of coolant channels. Further, the assembly is configured to cause simultaneously a coolant flow through the proximal heat exchanger and the distal heat exchanger, such that the first axial component and the second axial component are opposite to each other.

In use, the esophagus catheter may be inserted into the esophagus at a predetermined position within the esophagus. It is possible that, during use of the esophagus catheter, the distal heat exchanger is positioned substantially below the level of the heart of a person and the proximal heat exchanger is positioned substantially at or above the level of the heart of the person. As a result, the first axial component of the coolant flow within the proximal heat exchanger may be opposite to the flow direction of blood within the aorta, in particular the cerebral vessels and thoracic aorta. Likewise, the second axial component of the coolant flow within the distal heat exchanger may be opposite to the flow direction within the aorta, in particular the descending aorta. In case the esophagus catheter is positioned as described, an efficient heat exchange is effectuated with the proximal heat exchanger as well as with the distal heat exchanger, leading to efficient controlling of the temperature, for instance cooling of at least the brain of the person.

A plurality of coolant channels may be formed by an ascending leg and a descending leg of a continuous U-shaped conduit.

In a preferred embodiment, a first part of the plurality of coolant channels opens into the proximal heat exchanger at a proximal end thereof and opens into the distal heat exchanger at a distal end thereof, and a second part of the plurality of coolant channels opens into the proximal heat exchanger at a distal end thereof and opens into the distal heat exchanger at the proximal end thereof. In this way, it is provided that the coolant within the proximal heat exchanger flows from the proximal end to the distal end of the proximal heat exchanger or vice versa. Likewise, the coolant within the distal heat exchanger flows from the distal end to the proximal end of the distal heat exchanger or vice versa, which depends on the first axial component of the coolant flow within the proximal heat exchanger. As a result, the esophagus catheter may be placed around the level of the heart and the flow direction of the coolant in the proximal heat exchanger may be opposite to the flow direction of blood in vicinity of the proximal heat exchanger and the flow direction of coolant in the distal heat exchanger also may be opposite to the flow direction of blood in vicinity of the distal heat exchanger. As a result, an efficient heat exchange between the coolant and blood may be accomplished.

It is noted that the coolant channels may open into the respective heat exchanger via plural openings. The plural openings may be positioned close to each other or may be divided over a circumference of one or more of the plurality of coolant channels.

At least a part of the plurality of coolant channels may be integrated in a wall of the esophagus catheter. As a result, an inner space of the esophagus catheter may be used for other purposes, for example to provide food to the person.

The assembly may comprise a ventilating device for ventilating the person during controlling the temperature, e.g. cooling of the part of the person. In case the assembly is used for controlling the temperature of the brain of the person for instance during and/or after a cardiac arrest, it may be advantageous to be able to ventilate that person. By providing an assembly which is capable of controlling the temperature, for instance cooling of and ventilating the person, it may be effectuated that plural lifesaving actions may be taken when a person is in cardiac arrest.

In a preferred embodiment, the ventilating device is provided with a balloon to control the temperature of, e.g. to cool, blood flowing within an area around the ventilating device. Usually, the ventilating device is placed in a neck area of the person to be ventilated. The right and left common carotid artery run through the neck area, in which blood flows towards the brain of the person. By providing the balloon in a neck area, the temperature of the blood within the left and right common carotid artery may be controlled when passing the balloon. Therefore, an improved controlling of the temperature, for instance cooling of the brain may be accomplished with such embodiment.

In an embodiment, the balloon of the ventilating device is provided with an inlet channel and/or an outlet channel for a coolant. Due to the inlet channel and/or the outlet channel, it may be possible to provide a desired amount of coolant into the balloon when the ventilating device is properly positioned in the neck area of the person. The balloon may be used to fixate the laryngeal mask with respect to the larynx.

It is noted that the esophagus catheter may be positioned next to the ventilating device or that the ventilating device comprises an additional channel through which the esophagus catheter may be inserted into the esophagus.

Further, it may be possible to circulate the coolant through the balloon continuously by providing coolant to the balloon via the inlet and withdrawing coolant from the balloon via the outlet. As a result, temperature controlling, e.g. cooling of the brain may be improved.

The esophagus catheter and the ventilating device may be connected with each other, at least during use. Therewith, it may be effectuated that both the esophagus catheter and the ventilating device stay in position with respect to each other.

In an embodiment, the ventilating device comprises a laryngeal mask and/or an endotracheal tube.

When the ventilating device comprises a laryngeal mask, the esophagus catheter may be used as a stylet to position the laryngeal mask within the larynx.

In an embodiment, the esophagus catheter is formed as a unit with at least one of the laryngeal mask and the endotracheal tube, wherein the balloon is in fluid communication with the proximal heat exchanger and/or the distal heat exchanger of the esophagus catheter.

The esophagus catheter may extend in longitudinal direction beyond the distal heat exchanger and/or may comprise a lumen and/or an aperture for inserting a medical device, such as an ultrasound probe. It is advantageous that the medical device may be inserted into the esophagus of the person of which the temperature is controlled, for instance being cooled, such that it is for example possible to monitor a heart function of the person by means of Doppler monitoring. In case an ultrasound probe is inserted into the lumen, the coolant may provide an improved ultrasound guidance, leading to improved ultrasound imaging or in case the ultrasound probe is positioned between the proximal heat exchanger and the distal heat exchanger, the ultrasound probe is positioned for reliable measuring or determining of a cardiac output of the heart of the person. The esophagus catheter may serve as a guide wire for the medical device, for instance an ultrasound probe. In an embodiment comprising the laryngeal mask, the lumen may extend through the laryngeal mask.

In a further embodiment, the esophagus catheter may be used as a gastric tube. In this embodiment, when the esophagus catheter is placed in the esophagus, the esophagus catheter may extend from the distal end of the distal heat exchanger towards the stomach of the person. The esophagus catheter might have an aperture in a distal end thereof.

It is noted that in an embodiment one or more apertures might be provided in a wall of the esophagus catheter proximal to the proximal heat exchanger, between the proximal heat exchanger and the distal heat exchanger, and/or distal to the distal heat exchanger, as well as at or near a proximal end or at or near a distal end of the esophagus catheter.

In an aspect the invention provides for an esophagus catheter for controlling a temperature, e.g. cooling, of at least a part of a person, in particular the brain of the person, for example during or after a cardiac arrest, the esophagus catheter extending along a longitudinal axis and comprising a first heat exchanger defining a flow direction having a first axial component relative to the longitudinal axis, e.g. a first balloon, to be inserted into the esophagus of the person for controlling a temperature, e.g. cooling. The esophagus catheter further comprises a plurality of coolant channels, wherein at least a part of the coolant channels is in fluid communication with the first heat exchanger. The esophagus catheter is configured to cause a coolant flow through the first heat exchanger, such that the first axial component is directed from a proximal end to a distal end of the first heat exchanger.

The esophagus catheter may comprise a second heat exchanger defining a flow direction having a second axial component, e.g. a second balloon, wherein the second heat exchanger is placed distally to the first heat exchanger.

In an embodiment at least a part of the plurality of coolant channels is in fluid communication with the second heat exchanger, the esophagus catheter being configured to cause a coolant flow through the first heat exchanger and the second heat exchanger. In a more specific embodiment, the esophagus catheter is configured to cause simultaneously the coolant flow through the first heat exchanger and through the second heat exchanger, such that the second axial component is opposite relative to the first axial component.

In an aspect the invention provides for a method for controlling a temperature, e.g. cooling, of at least a part of a person, in particular the brain of the person, for example during or after a cardiac arrest, the method comprising steps of inserting an esophagus catheter into an esophagus of a person, the esophagus catheter extending along a longitudinal axis and comprising a proximal heat exchanger defining a first flow direction having a first axial component to the longitudinal axis, e.g. a proximal balloon, and a second heat exchanger defining a second flow direction having a second axial component to the longitudinal axis, e.g. a distal balloon; providing a coolant to the proximal heat exchanger balloon and the distal heat exchanger; and causing simultaneously a coolant flow through the proximal heat exchanger and through the distal heat exchanger, such that the first axial component and the second axial component are opposite to each other.

Aspects of the invention will be explained in greater detail by reference to exemplary embodiments of the invention shown in the drawings, in which:

FIG. 1 illustrates a schematic overview of a first embodiment of an assembly;

FIGS. 2A-C schematically illustrate aspects of the first embodiment as illustrated in FIG. 1;

FIG. 3 illustrates a top view of the first embodiment of the assembly of FIG. 1;

FIG. 4 illustrates a cross-section of the assembly of FIG. 3 according to line IV-IV;

FIG. 5 illustrates a partial cross-section of the assembly of FIG. 4 according to line V;

FIG. 6 illustrates in more detail a cross-section of a part of FIG. 3 according to line VI;

FIG. 9 illustrates a schematic overview of a ventilating device according to a second embodiment of the assembly;

FIG. 10 illustrates a cross-section according to line X-X in FIG. 9;

FIG. 11 illustrates a more detailed cross-section of a part of FIG. 9 according to line XI; and FIG. 12 illustrates an embodiment of an esophagus catheter.

Figure 7:
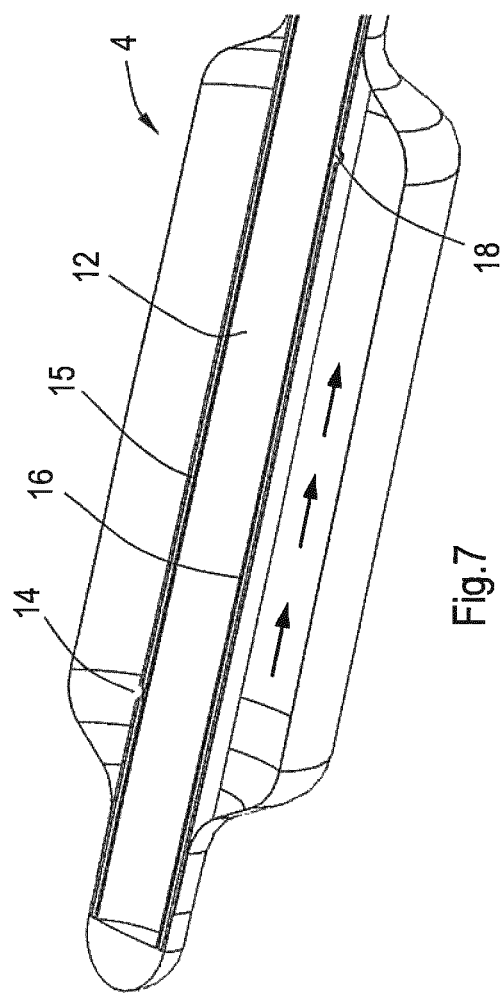
FIG. 7 illustrates a cross-section of the distal balloon of the first embodiment.

It should be appreciated, however, that these embodiments may not be construed as limiting the scope of protection for the present invention.

A first embodiment of an assembly 1 as presently provided is shown in FIG. 1. The assembly 1 comprises an esophagus catheter 2 and a laryngeal mask 3. A laryngeal mask 3 is a type of oropharyngeal airway that provides an alternative to endotracheal intubation and standard mask anaesthesia. The laryngeal mask 3 may be introduced into the hypopharynx to form a seal around the larynx, thereby permitting spontaneous or positive pressure ventilation without penetration of the larynx or esophagus. The laryngeal mask 3 is provided with a balloon 6 in order to be able to control the temperature of, e.g. to cool the larynx (not shown) or at least the area around the larynx. The balloon 6 is further intended to close off the trachea, such that the person may be ventilated by means of the laryngeal mask. Since the left and right common carotid artery run through the neck area and past the larynx, or at least through the area about the larynx, the temperature of the left and right common carotid artery may be controlled by the balloon 6 provided at the laryngeal mask 3. As a result of controlling the temperature of the blood flowing through the left and right common carotid artery, the temperature of the brain of the person may be controlled, for instance be lowered.

Further, air used for ventilating the person enters the lungs, thereby passing the laryngeal mask 3 with the balloon 6. When the air passes the balloon 6, the temperature of the air may be controlled, for instance lowered. Thus, air that reaches the lungs of the person may be cooled. Therefore, heat exchange between the air and the blood within the lungs will occur.

The esophagus catheter 2 is provided with a distal heat exchanger, such as a distal balloon 4 and a proximal heat exchanger, such as a proximal balloon 5. As can be seen in FIG. 1, the esophagus catheter extends into a longitudinal direction A. In this embodiment, the esophagus catheter 2 is connected to the laryngeal mask 3, and the laryngeal mask 3 and the esophagus catheter 2 are in fluid communication. A coolant within the proximal balloon 5 flows from a proximal end of the proximal balloon 5 towards a distal end of the proximal balloon 5 along an inner wall of the proximal balloon 5, as is indicated in FIG. 2B with arrow B. Arrow B represents the first axial component of the coolant flow through the proximal heat exchanger 5, i.e. the proximal balloon 5. The coolant within the distal balloon 4 flows from a distal end of the distal balloon 4 towards a proximal end of the distal balloon 4 along an inner wall of the distal balloon 4, as is indicated in FIG. 2C with arrow C. Arrow C represents the second axial component of the coolant flow through the distal heat exchanger 4, i.e. the proximal balloon 4. Thus, the flow direction of the coolant in the proximal balloon 5 along the inner wall 21 thereof is opposite to the flow direction of the coolant in the distal balloon 4 along the inner wall 22 thereof.

In use the esophagus catheter 2 is placed inside the esophagus (not shown) at a predetermined position. The distal balloon 4 may be positioned substantially below a level of the heart of the person. The proximal balloon 5 for instance may be positioned at the level of the heart. The proximal balloon 5 and the distal balloon 4 are filled with a coolant, such that the esophagus and the surrounding area, including blood flowing through that area, may be cooled. As a result, the flow direction of the coolant in the proximal balloon 5 is opposite to the flow direction of blood in the cerebral vessels and thoracic aorta. The flow direction of the coolant in the distal balloon 4 is opposite to the flow direction in the descending aorta. When the esophagus catheter 2 is positioned as described, an efficient heat exchange is effectuated with the proximal balloon 5 as well as with the distal balloon 4, in this embodiment leading to efficient cooling of at least the surrounding tissue and blood and therewith of the brain of the person.

The laryngeal mask 3 further comprises a tube 7 in order to connect inter alia the balloon 6 of the laryngeal mask with the environment when the assembly 1 is positioned within a person. An inlet channel 8 for a medical device (not shown) and a ventilating channel 9 run through the tube 7, in order to be able to ventilate the person of which the temperature is controlled, for instance lowered and to insert a medical device, such as an ultrasound probe (not shown) into the assembly 1. In use, when the ultrasound probe is inserted into the assembly 1, the ultrasound probe may be located at the level of the proximal balloon 5. At this position, the ultrasound probe is useable to monitor a function of the heart of the person. Since the ultrasound probe may be inserted into the lumen, the coolant may provide an improved ultrasound guidance, leading to improved ultrasound imaging.

It is noted that the tube 7 may be cooled and/or may be provided with coolant too.

FIGS. 3-5 show the assembly 1 of FIG. 1 in more detail. As can be seen in FIG. 3, the inlet tube 8 and the lumen 12, which are interconnected, for the medical device (not shown) extend through the laryngeal mask 3, the balloon 6, and the proximal balloon 5 of the esophagus catheter to the distal end of the distal balloon 4 of the esophagus catheter 1. The ventilating channel 9 opens within the circular balloon 6, such that air may be forced into the lungs of the person.

Further, an inlet channel 10 and an outlet channel 11 are connected to the balloon 6. The inlet channel 10 and the outlet channel 11 are intended to provide coolant to the balloon 6, and to let coolant out of the balloon 6, as is indicated in FIG. 2A. The inlet channel 10 and/or the outlet channel can be connected or connectable to a coolant pump (not shown), such as a fluid pump or a syringe.

As can be seen in FIG. 5, the balloon 6 is in fluid communication with a plurality of coolant channels comprising a first coolant channel 15 and a second coolant channel 16 of the esophagus catheter 2. Thus, a coolant may be inserted into the balloon 6 of the laryngeal mask 3 via inlet channel 10. When the coolant has entered the balloon 6, it may enter the first coolant channel 15 of the esophagus catheter 2. The first coolant channel 15 of the esophagus catheter 2 opens into the proximal balloon 5 at the proximal end thereof via opening 13 and into the distal balloon 4 at the distal end thereof via opening 14.

The proximal balloon 5 comprises an outlet opening 17 located at the distal end of the proximal balloon 5. The outlet opening 17 opens into the second coolant channel 16, which is in fluid communication to the balloon 6. The coolant within the proximal balloon 5 may leave the proximal balloon 5 via the outlet opening 17 into the second coolant channel 16. Thereafter, the coolant enters the balloon 6 and, eventually, the coolant leaves the balloon 6 via outlet channel 11.

The distal balloon 4 comprises an outlet opening 18 located at the proximal end of the distal balloon 4. The outlet opening 18 opens into the second coolant channel 16, which is connected to the balloon 6 and the proximal balloon 5. The coolant may leave the balloon 6 via outlet channel 11 as described above.

In FIG. 6, a cross-section of a part of FIG. 3 according to line VI is shown in more detail. The distal end of the proximal balloon 4 and the proximal end of the distal balloon 4 are shown. As can be seen, the proximal balloon 5 as well as the distal balloon 4 are provided around the lumen 12. The first coolant channel 15 and the second coolant channel 16 are integrated in a wall of the lumen 12. The second coolant channel 16 comprises an opening 17 located at the distal end of the proximal balloon 5, and an opening 18 located at the proximal end of the distal balloon 4. Both the opening 17 and opening 18 are intended for leaving coolant out of the proximal balloon 5 and the distal balloon 4, respectively.

A cross-section of the distal balloon 4 of the first embodiment is shown in FIG. 7. As can be seen, the distal balloon 4 is provided around the lumen 12. Within the wall of lumen 12, the first coolant channel 15 and the second coolant channel 16 are provided. The first coolant channel 15 opens into the distal balloon 4 via opening 14, which is located at the distal end of the distal balloon 4. The second coolant channel 16 opens into the distal balloon 4 via opening 18, which is located at the proximal end of the distal balloon 4. Thus, in use the coolant enters the distal balloon 4 via opening 14 and leaves the distal balloon 4 via opening 18. The coolant thus flows from the distal end to the proximal end of the distal balloon 4 along an inner wall 22 thereof, as indicated with arrows.

Figure 8:
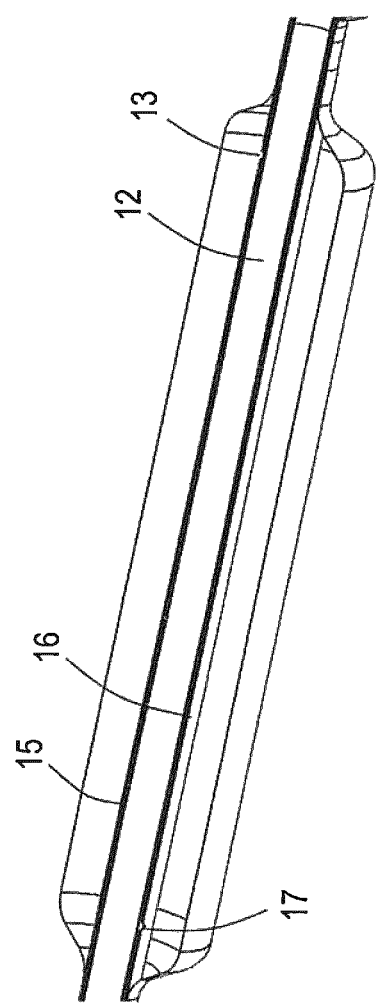
FIG. 8 illustrates a cross-section of the proximal balloon of the first embodiment.

A cross-section of the proximal balloon 5 of the first embodiment is shown in FIG. 8. As can be seen, the proximal balloon 5 is provided around the lumen 12. The first coolant channel 15 and the second coolant channel 16 are integrated in the wall of the lumen 12. The first coolant channel 15 opens into the proximal balloon 5 via opening 13, which is located at the proximal end of the proximal balloon 5. The second coolant channel 16 opens into the proximal balloon 5 via opening 17, which is located at the distal end of the proximal balloon 5. Thus, in use the coolant enters the proximal balloon 5 via opening 13 and leaves the proximal balloon 5 via opening 17. The coolant flows from the proximal end to the distal end of the proximal balloon 5 along an inner wall 21 thereof, as indicated with arrows.

FIG. 9 shows a ventilating device 3 according to a second embodiment of the assembly 1. In this embodiment, the ventilating device comprises an endotracheal tube 3. The endotracheal tube 3 comprises a ventilating tube 9 in order to be able to supply air to lungs of a person. A balloon 6 is provided at the distal end of the endotracheal tube 3. The balloon 6 is intended to be inserted into an airway of the person to be ventilated, and is inflated after being positioned within the airway, such that the endotracheal tube 3 is kept in position during ventilation.

The balloon 6, which might be inflatable, may be filled with a coolant. The coolant can be provided via inlet channel 15, which is accessible from outside the assembly 1. The balloon 1 can be inflated by supplying the coolant to the balloon. The coolant can be let out of the balloon 6 via outlet channel 16, which is also accessible from outside the assembly 1. As can be seen in FIG. 10, the inlet channel 15 and the outlet channel 16 are integrated in a wall of the ventilating tube 9.

A cross-section of the balloon 6 is shown in more detail in FIG. 11. As can be seen, the balloon 6 is provided around the ventilating tube 9. The inlet channel 15 opens into the balloon 6 via opening 19 and the outlet channel 16 opens into the balloon 6 via opening 20. Coolant can be circulated within the balloon 6 by introducing the coolant into the balloon 6 via opening 19 and withdrawing the coolant from the balloon 6 via opening 20. Thus, in this embodiment, the coolant is circulated from the proximal end of the inflatable balloon 6 to the distal end thereof. In this way, the flow direction within the balloon 6 is in counterflow to the flow direction of blood flowing towards the brain of a person.

It is noted that it is possible to use the inlet channel 15 as an outlet channel and vice versa, such that the flow direction of the coolant within the inflatable balloon 6 may be inverted.

FIG. 12 shows a second embodiment of the esophagus catheter. In this embodiment, the esophagus catheter 2 comprises a first heat exchanger, such as a proximal balloon 5, a second heat exchanger, such as a distal balloon 4 and a lumen 12 to insert a medical device into the esophagus catheter 2. The flow direction within the proximal balloon 5 is from the proximal end to the distal end of the proximal balloon 5, which is the first axial component of the coolant flow within the proximal balloon 5, along the inner wall 21 thereof. The flow direction within the distal balloon 4 is from the distal end to the proximal end of the distal balloon 4, which is the second axial component of the coolant flow within the distal balloon 4, along the inner wall 22 thereof. The flow directions along the inner wall of the proximal balloon 5 and the distal balloon 4 are thus opposite to each other.

It is noted that it is possible that the endotracheal tube 3 and the esophagus catheter 2 are connected to each other, at least during use. Thus, they may be inserted into the patient separately and thereafter be connected to each other.

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral.

The invention is not restricted to the above-described embodiments, which can be varied in a number of ways within the scope of the claims. It is for example possible that all balloons, i.e. the distal balloon, the proximal balloon and the balloon, are inflatable.

It is further possible that a flow within a proximal balloon and a flow within a distal balloon are adjustable separately, for instance for adjusting a pressure within each of the proximal balloon and the distal balloon separately. To be able to use a coolant in the proximal balloon with a temperature different from the temperature of the coolant in the distal balloon, it may be possible that a coolant circulation circuit of the proximal balloon is separated from a coolant circulation circuit of the distal balloon, i.e. the distal balloon has a first coolant channel and a second coolant channel and the proximal balloon has a first coolant channel and a second coolant channel which are separated from the channels of the distal balloon.

Further, it is noted that the assembly and/or the esophagus catheter may be used to warm up a person and/or may be used to keep a body temperature of a person at a predetermined level for instance during surgery.

The invention claimed is:

1. An assembly for cooling at least a part of a person including a brain of the person, the assembly comprising:
    an esophagus catheter to be inserted into an esophagus of the person for temperature control, the esophagus catheter extending along a longitudinal axis, the esophagus catheter comprising a proximal heat exchanger, and a distal heat exchanger and having a length so that the proximal heat exchanger and the distal heat exchanger are both positionable in the esophagus below a level of a larynx of the person, the proximal heat exchanger being a proximal balloon having a proximal end and a distal end and the distal heat exchanger being a distal balloon having a proximal end and a distal end,
    the esophagus catheter further comprising a plurality of coolant channels including at least an inlet coolant channel and an outlet coolant channel each of the inlet and outlet coolant channels are in fluid communication with the proximal heat exchanger and the distal heat exchanger, and
    a coolant pump connected to at least one of the plurality of coolant channels, and
    the assembly further being configured to simultaneously cause coolant flow through the proximal heat exchanger in a first direction and coolant flow through the distal heat exchanger in a second direction that is opposite the first direction, wherein coolant flow in the proximal heat exchanger is in the first direction from a proximal end to a distal end and wherein coolant flow in the distal heat exchanger is in the second direction from a distal end to a proximal end.

2. The assembly according to claim 1, wherein a first part of the inlet coolant channel opens into the proximal heat exchanger at a proximal end thereof and a second part of the inlet coolant channel opens into the distal heat exchanger at a distal end thereof, and wherein a first part of the outlet coolant channel opens into the proximal heat exchanger at a distal end thereof and a second part of the outlet coolant channel opens into the distal heat exchanger at a proximal end thereof such that coolant flows from the proximal end to the distal end in the proximal heat exchanger and flows from the distal end to the proximal end in the distal heat exchanger.

3. The assembly according to claim 1, wherein at least a part of the inlet and outlet coolant channels are integrated in a wall of the esophagus catheter.

4. The assembly according to claim 1, further comprising a ventilating device for ventilating the person during the cooling of the at least part of the person including the brain of the person.

5. The assembly according to claim 4, wherein the ventilating device is provided with a balloon to cool blood flowing within an area around the ventilating device.

6. The assembly according to claim 5, wherein the balloon of the ventilating device is provided with an inlet channel and/or an outlet channel for a coolant.

7. The assembly according to claim 4, wherein the esophagus catheter and the ventilating device are connected with each other, at least during use.

8. The assembly according to claim 4, wherein the ventilating device comprises a laryngeal mask and/or an endotracheal tube.

9. The assembly according to claim 8, wherein the esophagus catheter is formed as a unit with at least one of the laryngeal mask and the endotracheal tube, wherein a balloon of the ventilating device is in fluid communication with at least one of the proximal heat exchanger and the distal heat exchanger.

10. The assembly according to claim 8, wherein the esophagus catheter further comprises a lumen and/or an aperture for inserting an ultrasound probe, and wherein, when the ventilating device comprises a laryngeal mask, the lumen extends through the laryngeal mask, at least during use.

11. An esophagus catheter for cooling at least a part of a person including a brain of the person, the esophagus catheter to be inserted into an esophagus of the person, extending along a longitudinal axis and comprising:
    a first heat exchanger being a first balloon,
    a second heat exchanger being a second balloon, wherein the second heat exchanger is distal to the first heat exchanger, wherein a length of the esophagus catheter is such that the first heat exchanger and the second heat exchanger are both positionable in the esophagus below a level of a larynx of the person, the first heat exchanger is positionable in the esophagus above a level of a heart of the person and the second heat exchanger is spaced apart from the first heat exchanger so the second heat exchanger is positionable in the esophagus below the level of the heart of the person,
    a plurality of coolant channels comprising an inlet coolant channel in fluid communication with the first heat exchanger and the second heat exchanger and an outlet coolant channel in fluid communication with the first heat exchanger and the second heat exchanger,
    the esophagus catheter being configured to cause a coolant flow in the inlet and outlet coolant channels, through the first heat exchanger in a first flow direction having a first axial component relative to the longitudinal axis and the second heat exchanger in a second flow direction having a second axial component relative to the longitudinal axis, and
    wherein the inlet coolant channel has a first inlet opening that opens into a proximal end in the first heat exchanger and a second inlet opening into a distal end in the second heat exchanger and the outlet coolant channel has a first outlet opening into a proximal end of the second heat exchanger and a second outlet opening into a distal end of the first heat exchanger so that coolant flows simultaneously through the first heat exchanger and the second heat exchanger in opposite directions, and the first axial component is directed from the proximal end to the distal end of the first heat exchanger and the second axial component is directed from the distal end to the proximal end of the second heat exchanger.

12. The esophagus catheter according to claim 11, further comprising a ventilating device for ventilating the person during the cooling of at least the part of the person including the brain of the person.

13. The esophagus catheter according to claim 12, wherein the ventilating device comprises a laryngeal mask and/or an endotracheal tube and the esophagus catheter is formed as a unit with at least one of the laryngeal mask and/or the endotracheal tube.

14. The esophagus catheter according to claim 12, wherein the ventilating device is provided with a balloon to cool blood flowing within an area around the ventilating device and the balloon of the ventilating device is in fluid communication with the coolant in at least one of the first heat exchanger and the second heat exchanger.

15. The esophagus catheter of claim 11, further comprising a lumen and/or aperture configured for receiving a medical device.

16. The esophagus catheter of claim 15, wherein the medical device comprises an ultrasound probe.

17. A method of cooling at least a part of a person including a brain of the person, the method comprising:
   inserting an esophagus catheter into an esophagus of the person, the esophagus catheter extending along a longitudinal axis and including a proximal heat exchanger comprising a proximal balloon and a distal heat exchanger comprising a distal balloon,
   positioning the esophagus catheter such that the proximal and distal balloons are located below a level of a larynx of the person and the proximal balloon is located at or above a level of a heart of the person and the distal balloon is located below the level of the heart of the person,
   providing a coolant to the proximal heat exchanger and the distal heat exchanger, and causing simultaneously a coolant flow through the proximal heat exchanger and through the distal heat exchanger, and
   wherein the coolant is provided to the proximal heat exchanger and the distal heat exchanger through an inlet coolant channel having a first inlet opening that opens into a proximal end of the proximal heat exchanger and a second inlet opening that opens into a distal end of the distal heat exchanger and exits the proximal heat exchanger and the distal heat exchanger through an outlet coolant channel having a first outlet opening that opens into a proximal end of the distal heat exchanger and a second outlet opening that opens into a distal end of the proximal heat exchanger such that a first flow direction in the proximal heat exchanger is directed from the proximal end to the distal end of the proximal heat exchanger and opposite to a second flow direction in the distal heat exchanger that is directed from the distal end to the proximal end of the distal heat exchanger.

18. The method of claim 17, further comprising inserting a ventilating device into an airway of the person during the cooling of at least the part of the person including the brain of the person, wherein the ventilating device is located proximal to the proximal and distal heat exchangers and is provided with a balloon, wherein causing simultaneously the coolant to flow through the balloon of the ventilating device through the proximal heat exchanger and through the distal heat exchanger.

19. The method of claim 17, further comprising inserting a medical device into a lumen and/or aperture of the esophagus catheter to monitor functions of the person.

20. The method of claim 19, wherein the medical device comprises an ultrasound probe to provide ultrasound imaging and guidance and to measure cardiac output of the heart of the person.

* * * * *